United States Patent [19]
Johnsen

[11] Patent Number: 5,324,949
[45] Date of Patent: Jun. 28, 1994

[54] METHOD OF EFFECTING NIR-ANALYSES OF SUCCESSIVE MATERIAL SAMPLES, AND A SYSTEM FOR CARRYING OUT THE METHOD

[75] Inventor: Erik Johnsen, Vejle, Denmark
[73] Assignee: Jesma-Matador A/S, Vejle, Denmark
[21] Appl. No.: 576,505
[22] PCT Filed: Mar. 29, 1989
[86] PCT No.: PCT/DK89/00070
§ 371 Date: Oct. 7, 1991
§ 102(e) Date: Oct. 7, 1991
[87] PCT Pub. No.: WO89/09388
PCT Pub. Date: Oct. 5, 1989

[30] Foreign Application Priority Data
Mar. 29, 1988 [DK] Denmark .................. 1720/88

[51] Int. Cl.⁵ .................. G01N 21/01; G01N 21/47
[52] U.S. Cl. .................. 250/341; 250/339.01
[58] Field of Search .................. 359/507; 250/328, 341, 250/358.1, 339; 356/445

[56] References Cited

U.S. PATENT DOCUMENTS

| | | | |
|---|---|---|---|
| 3,328,587 | 6/1967 | Brown et al. | 250/358.1 |
| 3,677,652 | 7/1972 | Little | 250/343 |
| 3,869,213 | 3/1975 | Green | 356/244 |
| 4,563,581 | 1/1986 | Perten | 250/341 |
| 4,640,614 | 3/1987 | Roberts et al. | 250/341 |
| 4,742,228 | 5/1988 | Bischoff | 250/341 |
| 4,991,949 | 2/1991 | Moorehead | 359/507 |

FOREIGN PATENT DOCUMENTS 8303817  4/1988  Sweden .

Primary Examiner—Carolyn E. Fields
Attorney, Agent, or Firm—Antonelli, Terry, Stout & Kraus

[57] ABSTRACT

With the present invention, the NIR-technique is utilized for a fully automatic on-line analyzing of successive samples, viz. with the use of a test chamber which is built together with the optical unit and is open towards this unit through a restricted side opening. The test chamber has a volume which is much larger than that of the known test cups, whereby the remnant-pollution of the following sample can be kept at an acceptable low level, without the test chamber having to be totally cleaned each time. A particularly critical area, however, is the material area just next to the optical unit, and remnants at this place must by necessity be removed. The present invention provides for a complete avoidance of such remnant deposits, in that between the side opening of the test chamber and the optical unit, there is placed a transparent, thin separation film, which between successive operations is advanced for removal of the last used film area and for delivery of a new and entirely clean film area to the critical area.

8 Claims, 2 Drawing Sheets

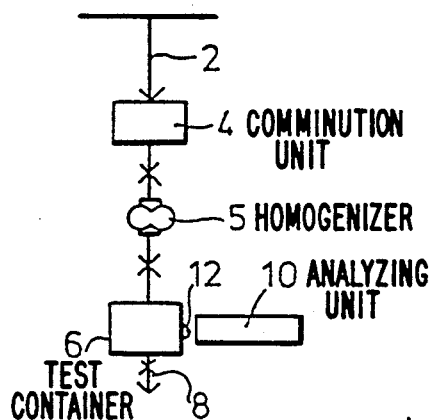
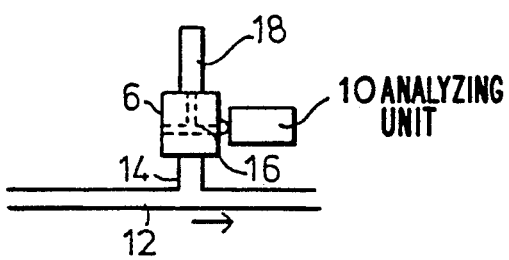
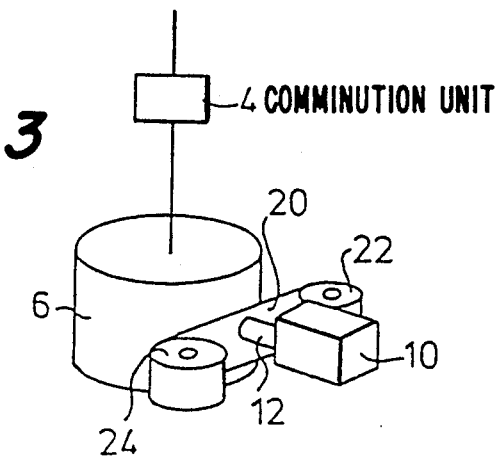
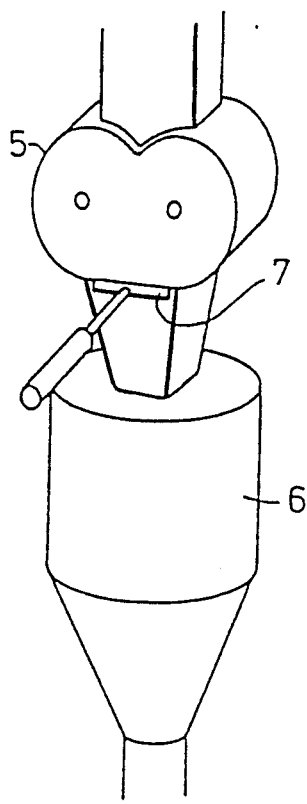
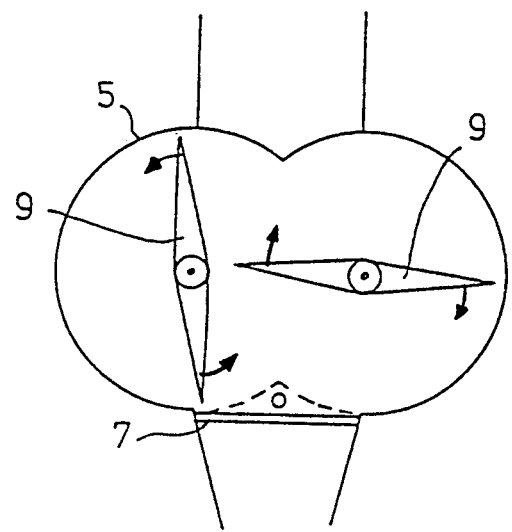

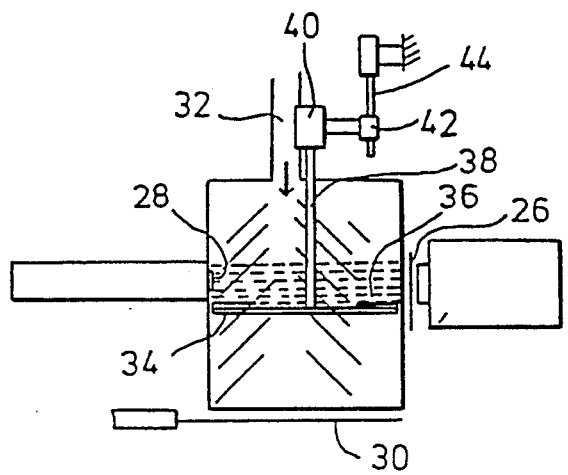
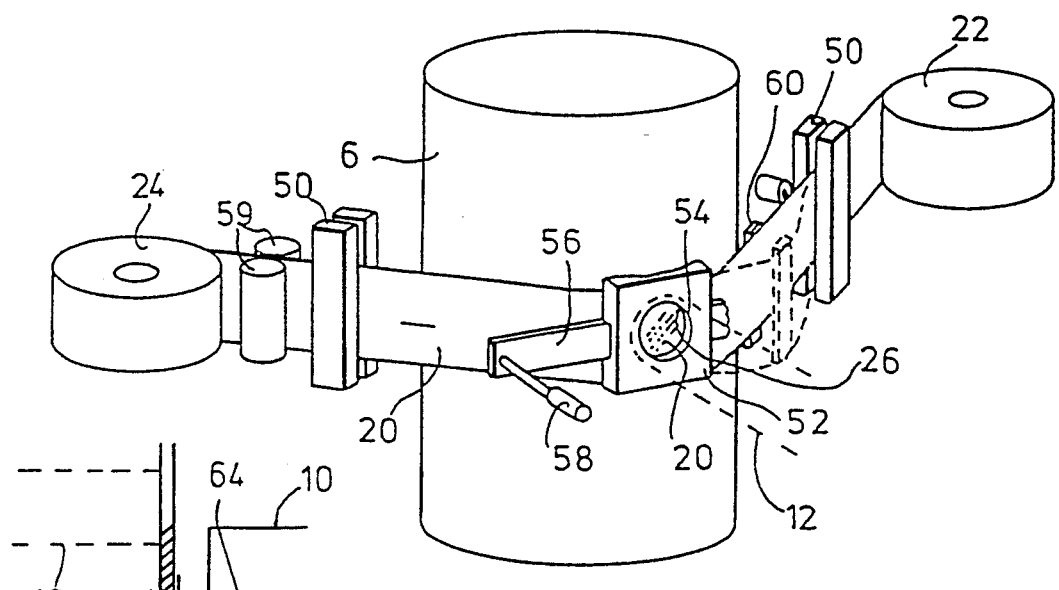
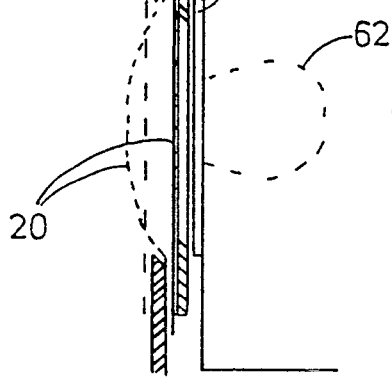

METHOD OF EFFECTING NIR-ANALYSES OF SUCCESSIVE MATERIAL SAMPLES, AND A SYSTEM FOR CARRYING OUT THE METHOD

FIELD OF THE INVENTION

The present invention relates to a method of carrying out analyses of materials by the NIR-principle or corresponding principles of analysis.

BACKGROUND OF THE INVENTION

NIR stands for Near Infrared Reflection and designates a method of analysis, in which the contents of various components of materials, e.g., water and protein, can be determined by a quite brief infrared irradiation of a sample portion of a few grams of the material. NIR analysis devices for general laboratory applications, e.g., in feedstuff factories or mixing establishments, have already been developed.

In the use of such devices, a homogenized sample of a few cubic centimeters is placed in a particular test cup, which is then mounted against a quartz disc on an analyzer head of the device, from which the surface of the sample is irradiated; the reflected rays are picked up by a particular detector which supplies electrical signals representative of the various components of the material. Before the next analysis, the equipment must be cleaned carefully, usually by washing with an organic solvent, as remnants of the material sample in the test cup or on the quartz disc may cause the next analysis to be inaccurate.

SUMMARY OF THE INVENTION

Said method is very advantageous compared to conventional methods, but like conventional methods, said method has hitherto not been suited for a still more advantageous application, i.e., in connection with automatic on-line sample analysis and automatic process control. The present invention aims at providing a method and an apparatus for carrying out the method, which makes such an application possible, whereby it will be possible to perform analyses in rapid succession in a fully automatic manner.

According to the present invention, use of the small test cup is abandoned and instead a considerably larger test chamber is used in front of the analyzer head, it being recognized that in the desired manner of operation, it will be unrealistic to perform washings with organic solvents or other clean-up procedures between the analyses. Instead, an aim of use of a larger chamber is to make remnants from a preceding sample so proportionally insignificant that the inaccuracy caused thereby can be kept within practically acceptable limits.

It must be possible to introduce the material into the test chamber and to discharge the material from the test chamber in such a manner that successive samples can be analyzed with a reasonably high frequency in order that the least possible remnant of each sample is left in the test chamber. Particularly in the case of non-homogeneous solid substances, a suitable homogenization must be provided, that is, in such a manner that a successively used homogenizer ahead of the test chamber does not retain essential remnants of the treated material, which, could cause a considerable pollution of the subsequent sample portion or portions. In connection with the present invention, it has been realized that under these circumstances it will hardly be possible to operate with a real homogenization or fine grinding of the material, but also that the problem can be solved in another way which is discussed herein.

The radiation used in the analysis is reflected mainly from the surface of the sample material, but the rays have a certain depth of penetration into the material so that the area essential to the analysis will be the surface layer bearing against the quartz disc of the analyzer head, the thickness of said layer being larger or smaller depending upon the nature of the material; however, the thickness of said layer is generally only a few millimeters, which accounts for the fact that it has been possible to use quite small samples. At the same time, however, this also accounts for the fact that use of a relatively large test chamber, in which the thickness or depth of the material sample opposite the analyzer head is considerably increased, ensures that a possible remnant of the preceding sample portion at the rear wall of the test chamber opposite the analyzer head becomes of little or no importance to the result of the subsequent analysis.

In return, the problem remains that deposited remnants of the preceding sample portion on the quartz disc or window will manifest themselves strongly as a source of pollution during the analysis of the next sample, and this pollution may interference with the result of the analysis. Consequently, such pollution must necessarily be avoided, and according to the present invention, this is obtained by using a window which is a double layer window, of which the layer facing the test chamber is exchangeable with a new and clean layer after each discharge of a sample portion. Appropriately a thin, transparent film is used for this purpose, as the film can be made to lean on the quartz disc and, in addition, may be advanced stepwise as part of an automatically controlled cycle operation of the entire equipment. It is noted that the provision of a new and clean wall area by advancing a film across an opening in an analysis chamber is not moved per se, cf. U.S. Pat. No. 3,677,652, which, however, deals with occasional exchange of a window area of a gas analysis chamber where the analysis is carried out on the entire quantity of gas.

In handling finely cut solid matter material, problems with respect to separation adjacent to the measurement window may arise; to overcome the analysis errors caused thereby, use may be made, according to the present invention, of a particular "measure face homogenization" by means of a rotating arm which promotes a local mixing of the material at that area.

BRIEF DESCRIPTION OF THE DRAWINGS

The present invention will be explained in more detail in the following description with reference to the accompanying drawings, wherein FIG. 1 is a schematic picture of an analysis system for solid substances; and FIG. 2 is a corresponding picture of a system for analyzing samples of viscous materials; and FIG. 3 is a schematic perspective picture of the system shown in FIG. 1; and FIG. 4 is a perspective picture of a homogenizer used in the system; and FIG. 5 is a vertical sectional picture of the homogenizer of FIG. 4; and FIG. 6 is a cross section of the system shown in FIG. 3; and FIG. 7 is a more detailed perspective picture of FIG. 6; and FIG. 8 is a sectional picture of the analysis area of the system.

DETAILED DESCRIPTION

In FIG. 1, a supply line 2 for delivering granulated or fibrous solid matter material to a comminution unit 4 is shown, from which comminution unit, the material is delivered to a homogenizer 5 and then to a test container 6 having a bottom outlet 8 for successive discharge of material samples from the test container 6. A side area of said test container is provided with a measurement opening which is connected with an analyzing unit 10 through an analyzer head 12 thereon. By means of a suitable valve arrangement, provision is made for supplying material samples to the container, and discharging them from the container in as rapid succession as possible, each sample being subjected to an analysis by means of the unit 10.

FIG. 2 shows a corresponding system for successive analysis of a viscous substance which is conveyed through a pipe 12. This pipe has a branch pipe 14 leading to the test chamber 6, wherein in this embodiment, a piston 16 can be actuated up and down by means of an operating cylinder 18. Thus, by operating said cylinder, material can be pulled up from the pipe 12 for filling of the chamber 6 and pushed back to the pipe 12 for emptying of the chamber 6, respectively, whereby analyses of the viscous material conveyed through the pipe 12 can be performed at short intervals.

As shown in FIG. 3, a transverse film 20 may be fitted between a side opening in the test container 6 and the adjacent analyzer head 12, which film can be advanced between takeup and pay-off reels 22 and 24, which takeup and pay-off reels are preferably coupled together in a cassette-like fashion so as to be easily exchangeable.

The comminution unit 4 is preferably a cutting unit in the form of a cylindrical flow-through chamber, in which a knife rotor is fast rotating. In principle, a beater drum might be used, but it is desirable to retain as minimal remnants of the individual sample portions as possible in the comminution unit.

The homogenizer 5 is shown in a preferred embodiment in FIGS. 4 and 5. The homogenizer consists of a double rotor chamber with a bottom shutter 7 and contains a pair of substantially plate shaped wing rotors 9 which wing rotors are phase displaced 90° from each other and rotate in partial mesh with each other as shown in FIG. 5, whereby the wing rotors can homogenize the entire sample portion effectively, before the sample portion is discharged through the bottom of the homogenizer to flow down into the test container 6.

In FIG. 6, a piston 28 is mounted in the wall of the test chamber opposite the measurement aperture 26, which piston can be operated to push the material towards the area of the measurement opening, and the chamber is provided with a shutter 30 at the bottom. At the top, the supply of material to the chamber takes place through a pipe 32 from the cutting device 4. The cutting device is provided with fast rotating knives which are able to cut the material to a degree of fineness sufficient for a correct NIR-analysis of the material. Thus, as the material is cut, but not ground, the unit 4 can be arranged so that essential remnants of the sample portion to be delivered are not retained within the cutting device.

However, as indicated by slanting lines in FIG. 6, finely cut material, which is filled into the chamber 6, is deposited so as to form a certain stratification in the chamber, the material being not completely homogeneous, so that separation between finer and coarser components occurs. This stratification, even if it may be quite fine, can adversely affect the accuracy of the analysis; therefore, it is desirable to counteract or eliminate the stratification. This might be effected by a simple agitation; however, use of simple agitation may lead to other separation problems. According to the present invention, it has been found that the undesirable stratification can be broken by a surface or "face of measurement" homogenization wherein an agitation wing 34 with a slightly upturned outer portion 36 is rotated with low velocity by a shaft 38 which is simultaneously slowly elevated, so that the ends of the agitating wings move helically upwards through the material area next to the measurement aperture 26, the material being currently slightly raised locally and subsequently dropped behind the wing. By this means, the desired homogenization can be obtained without the occurrence of further separation problems.

Accordingly, as shown in FIG. 6, a motor 40 for driving the shaft 38 is mounted on a bracket 42, which in turn is mounted on a motor driven spindle 44 for vertical movement of the system 40, 38, 34. As soon as the wing 34 has reached its upper position opposite the top edge of the measurement opening 26, the piston 28 may be actuated and the analysis performed. If desired, the wing may be elevated all the way up by switching to fast operation of the spindle 44.

In FIG. 7, a more detailed example of an applicable guide of the film 20 is shown. This film passes through an arc along the smooth, curved wall of the test chamber 6 about the measurement opening 26, and along the free runs of the film. Between this area of contact and the reels 22 and 24, pairs 50 of clamping jaws are positioned, which are operable to clamp and release the film. Around and outside the edge area of the measurement opening and outside the contact area of the film, a thrust plate 52 is mounted, whose side facing the chamber 6 is shaped so as to correspond exactly to the surface shape of the chamber, said thrust plate having a central aperture 54 opposite the measurement opening 26, whereas the outer side of the plate 52 is quite flat. The thrust plate 52 is provided with a pair of oppositely extending side arms 56, which are connected to actuating cylinders 58 for pressing the plate against the wall of the test chamber. Just outside said plate, the analyzer head 12 is positioned. A mechanism for stepwise advance of the film is provided by a pair of driving rollers 59. These rollers are coordinated with the clamping jaws 50 and the thrust plate 52, such that in each cycle of operation, the film can be advanced freely and thereafter clamped.

In the embodiment of FIG. 7, clamping of the jaws 50 is first effected, whereupon a thrust beam 60 is positioned between said area of contact of the film and one set of clamping jaws is actuated to thereby push the film path out as shown in stippled lines. As the thrust plate 52 is not actuated, a stretching of the entire film along the length of its path between the pair of clamping jaw sets 50 will take place. The film having preferably a thickness of only about 0.05 mm is readily stretchable; however, being not supported opposite the measurement opening 26, the film will, as shown in FIG. 8, be caused to bulge inwardly into said opening. Thereupon the thrust plate 52 is actuated to effectively clamp the film against the chamber wall all the way around the measurement opening 26.

Said bulging of the film is desirable because the homogenizer wing 36 is then able to rotate freely in the test chamber, but still in the most critical area reach all the way out to the surface layer of the material at the measurement opening 26, the wing ends being enabled to "lick" across the bulged film under slight local pressing out of the film, in any case, at the central area of the bulge. The measurement opening may have a diameter of about 50 mm, but the area of measurement will typically be a circular, central area with a diameter of 10-22 mm, i.e., a good "measurement face homogenization" will be obtainable in any case in this important area. The active optic head of the analyzer unit is shown in stippled line by 62 in FIG. 8.

When the homogenizer wing 36 has been removed and the piston 28 (FIG. 6) is actuated, the sample material will push the film bulge outwards, i.e., the film bulges out through the aperture 54 in the thrust plate 52 into engagement with the quartz disc 64, FIG. 8, of the analyzer head, whereby a reliable analysis can be performed.

Thereafter, the piston 28 is withdrawn and the material is discharged from the chamber 6. The film 20 may be advanced one step; however, this advance should be delayed as much as possible, so that dust from the sample portion has time to fall down, before the new, clean film area is supplied to the measurement opening. This also applies, if in connection with or after the discharge of material, a compressed-air flushing of the test chamber and the wing system 36, 38 is effected by means of appropriately shaped and positioned nozzles not shown.

The thrust plate 52 prevents leakage of sample material between the inner side of the film and the outer side of the test chamber and hence, against pollution caused thereby of the measurement area which might interfere with the next sample portion; otherwise such pollution might very well occur during the advance of the film. As mentioned, the thrust plate must be movable to clamp and release the film, which requires a certain additional spacing between the wall of the test chamber and the quartz disc 64. In systems where this spacing tends to be undersirably large, it will be possible to make the test chamber and the entire analyzer 10 so mutually movable that they can be moved towards each other after the film advance; it may even be desirable to have the thrust plate 52 firmly mounted on the analyzer.

As to the system shown in FIG. 2, particularly referring to pumpable media which will usually be fully homogenized or, for the analysis of material which is sufficiently homogenized, it will normally be unnecessary to use the particular homogenizer wing 36, so that there will be no associated need of producing the mentioned film bulging through the measurement opening.

Still, a certain bulging in will be desirable after the short period of analysis, in which the pressure of the material produces a bulging out of the film against the quartz disc 64, in as much as control of the pressure so as to cause subsequent bulging in of the film will bring along the affect that the piston 16 during a return movement for bringing the sample portion back to the pipe 12 will scrape downwards across the material adhering to the film; thus, during the next film advance there will be a substantially reduced quantity of adhering material, which by being carried away from the area in connection with the film advance may be deposited at the side edge of the measurement opening and possibly give rise to a pollution of the succeeding sample portion.

It will be understood that the piston 16 should be very accurately adapted to the test chamber 6, so that the piston can affect a practically complete discharge of all parts of the sample material from the chamber 6 in order to avoid pollution of the succeeding sample. An effective scraping clean of the inner wall of the test chamber and preferably, also an extensive scraping off of the material which is deposited in the measurement opening 26 itself outside the periphery of the piston 16 is also desired.

It will be understood that the present invention is not restricted to the embodiments shown, as the detailed described arrangements can be equated in various other ways. Likewise, it in not crucial to the invention that the applied analysis equipment operates just in accordance with the NIR-principle, as also other kinds of analysis are possible. Thus, it will be a possibility to use transillumination of the material instead of, or, in addition to, reflection irradiation; thus, an opening for the admission of crosswise radiation through the material can be provided wherein the opening is diametrically opposite from the measurement opening 26, in which case the additional opening should be covered by an advanceable film or possibly by a rotable disc which can be turned stepwise for successive supply of new, clean areas of faces of separation, possibly of the areas of said disc previously turned away from the area of measurement. In using such a technique the measurement opening should preferably be formed in a flat side portion of the test chamber.

It is noted the thrust plate 52 must not necessarily be movable by means of the cylinder 58, as particularly in connection with handling of solid materials it may be sufficient that the thrust plate is urged inwards against the outer side of the chamber or container 6 by means of suitable compression springs, not shown. In this case the spring force acting on the film needs not be too strong for the film to be advanced across the clamping area behind the thrust plate 52.

The volume of the test container may be for example 2-10 liters.

I claim:

1. A method for carrying out analyses of successive samples of solid or viscous material, the method comprising the steps of:
   supplying a sample to a test chamber, said test chamber being larger in volume than a volume of sample necessary for execution of the analysis, and being substantially stationary with respect to an analyzer head;
   bringing a surface area of said sample into a position against an exchangeable layer of a double layer window including a window of the analyzer head, said exchangeable layer being pressable against an outer side of the chamber around a wall opening of said test chamber, said wall-opening being positioned immediately opposite the window of the analyzer head, said wall opening being spaced from both ends of said test chamber, said sample in a region of the wall opening being larger in volume than a volume of the sample in said region necessary and sufficient for execution of the analysis;
   analyzing said sample through cooperation with said analyzer head by NIR infrared reflection of the sample;
   emptying the chamber;

cleaning the chamber and the double layer window to a required degree, said exchangeable layer facing the test chamber being consistently exchanged with a new and clean exchangeable layer between successive analysis operations using an automatically operating exchange mechanism; and supplying a new sample to be analyzed.

2. A method for carrying out analyses of successive samples of solid or viscous material, the method comprising the steps of:

supplying a sample to a test chamber, said test chamber being larger in volume than a volume of sample necessary for execution of the analysis, and being substantially stationary with respect to an analyzer head;

bringing a surface area of said sample into a position against an exchangeable layer of a double layer window including a window of the analyzer head, said exchangeable layer being pressable against an outer side of the chamber around a wall opening of said test chamber, said wall-opening being positioned immediately opposite the window of the analyzer head, said wall opening being spaced from both ends of said test chamber, said sample in a region of the wall opening being larger in volume than a volume of the sample in said region necessary and sufficient for execution of the analysis;

analyzing said sample through cooperation with said analyzer head by NIR infrared reflection of the sample;

emptying the chamber;

cleaning the chamber and the double layer window to a required degree, said exchangeable layer facing the test chamber being consistently exchanged with a new and clean exchangeable layer between successive analysis operations using an automatically operating exchange mechanism;

supplying a new sample to be analyzed, and wherein the exchangeable layer is made of a separating film of radiation transparent material, said method further comprising the step of automatically controlling the film to advance stepwise between each pair of succeeding analysis operation.

3. A method for carrying out analyses of successive samples of solid or viscous material, the method comprising the steps of:

supplying a sample to a test chamber, said test chamber being larger in volume than a volume of sample necessary for execution of the analysis, and being substantially stationary with respect to an analyzer head;

bringing a surface area of said sample into a position against an exchangeable layer of a double layer window including a window of the analyzer head, said exchangeable layer being pressable against an outer side of the chamber around a wall opening of said test chamber, said wall-opening being positioned immediately opposite the window of the analyzer head, said wall opening being spaced from both ends of said test chamber, said sample in a region of the wall opening being larger in volume than a volume of the sample in said region necessary and sufficient for execution of the analysis;

analyzing said sample through cooperation with said analyzer head by NIR infrared reflection of the sample;

emptying the chamber;

cleaning the chamber and the double layer window to a required degree, said exchangeable layer facing the test chamber being consistently exchanged with a new and clean exchangeable layer between successive analysis operations using an automatically operating exchange mechanism;

supplying a new sample to be analyzed;

comminuting solid material to be analyzed into finely cut material, said solid material being passed through a fine cutting device with rotating knives, from which the finely cut material flows down into the test chamber;

agitating the finely cut material by a rotating and elevating wing including outer end portions, wherein said end portions raise the material, which material subsequently falls down behind the wing, said wing being displaced axially while rotating for lifting an entire belt of material next to the wall opening; and homogenizing each sample immediately before introduction of each sample into the test chamber by passing each sample through a portion homogenizer.

4. A method for carrying out analyses of successive samples of solid or viscous material, the method comprising the steps of:

supplying a sample to a test chamber, said test chamber being larger in volume than a volume of sample necessary for execution of the analysis, and being substantially stationary with respect to an analyzer head;

bringing a surface area of said sample into a position against an exchangeable layer of a double layer window including a window of an analyzer head, said exchangeable layer being pressable against an outer side of the chamber around a wall opening of said test chamber, said wall-opening being positioned immediately opposite the window of the analyzer head, said wall opening being spaced from both ends of said test chamber, said sample in a region of the wall opening being larger in volume than a volume of the sample in said region necessary and sufficient for execution of the analysis;

analyzing said sample through cooperation with said analyzer head by NIR infrared reflection of the sample;

emptying the chamber;

cleaning the chamber and the double layer window to a required degree, said exchangeable layer facing the test chamber being consistently exchanged with a new and clean exchangeable layer between successive analysis operations using an automatically operating exchange mechanism supplying a new sample to be analyzed, and wherein the sample to be supplied is a fluid or viscous material, wherein the sample is supplied to the test chamber by movement of a piston closely fitting therein, and wherein the chamber is emptied by oppositely directed wall scraping movements of the piston.

5. An apparatus for carrying out analyses of successive samples of solid or viscous material, the apparatus comprising:

a substantially stationary test chamber, said test chamber being adapted to receive and deliver successive volumes of samples, said samples being subjected to an analysis by an analyzer head during passage of said samples through the test chamber;

a double layer window including a window of the analyzer head and an exchangeable layer, said chamber being placed adjacent to the window in the analyzer head said test chamber having a volume greater than the respective volumes of the sample necessary and sufficient for execution of an analysis, said exchangeable layer being consistently exchangeable between successive analysis operations;

a side opening positioned immediately opposite the analyzer head; and automatic control means for bringing about said exchanges, and wherein the analyzer head is an analyzer head of a NIR infrared reflection analyzer.

6. An apparatus, for carrying out analyses of successive samples of solid or viscous material, the apparatus comprising:

a substantially stationary test chamber, said test chamber being adapted to receive and deliver successive volumes of samples, said samples being subjected to an analysis by an analyzer head during passage of said samples through the test chamber;

a double layer window including a window of the analyzer head and an exchangeable layer, said chamber being placed adjacent to the window in the analyzer head said test chamber having a volume greater than the respective volumes of the sample necessary and sufficient for execution of an analysis, said exchangeable layer being consistently exchangeable between successive analysis operations;

a side opening positioned immediately opposite the analyzer head; and automatic control means for bringing about said exchanges, and wherein the analyzer head is an analyzer head of a NIR infrared reflection analyzer and wherein a wall of the test chamber comprises one or more nozzles for injection of cleaning air against areas in which the sample may be retained subsequent to the discharge of a preceding sample from the test chamber.

7. An apparatus for carrying out analyses of successive samples of solid or viscous material, the apparatus comprising:

a substantially stationary test chamber, said test chamber being adapted to receive and deliver successive volumes of samples, said samples being subjected to an analysis by an analyzer head during passage of said samples through the test chamber;

a double layer window including a window of the analyzer head and an exchangeable layer, said chamber being placed adjacent to the window in the analyzer head said test chamber having a volume greater than the respective volumes of the sample necessary and sufficient for execution of an analysis, said exchangeable layer being consistently exchangeable between successive analysis operations;

a side opening positioned immediately opposite the analyzer head; and automatic control means for bringing about said exchanges, wherein the analyzer head is an analyzer head of a NIR infrared reflection analyzer and wherein the test chamber is exactly cylindrical and said apparatus further comprises a piston which is displaceable for filling and emptying the chamber with viscous materials, the piston being adapted to effect a clean scraping of the cylindrical chamber wall at emptying.

8. An apparatus for carrying out analyses of successive samples of solid or viscous material, the apparatus comprising:

a substantially stationary test chamber, said test chamber being adapted to receive and deliver successive volumes of samples, said samples being subjected to an analysis by an analyzer head during passage of said samples through the test chamber;

a double layer window including a window of the analyzer head and an exchangeable layer, said chamber being placed adjacent to the window in the analyzer head, said test chamber having a volume greater than the respective volumes of the sample necessary and sufficient for execution of an analysis, said exchangeable layer being consistently exchangeable between successive analysis operations;

a side opening positioned immediately opposite the analyzer head;

automatic control means for bringing about said exchanges wherein the test chamber has a large volume greater than the volume of the sample which is necessary and sufficient for execution of the analysis for reducing interference caused by the presence of any remnants of a preceding sample, and wherein the analyzer head is an analyzer head of a NIR infrared reflection analyzer.

* * * * *

UNITED STATES PATENT AND TRADEMARK OFFICE
CERTIFICATE OF CORRECTION

PATENT NO. : 5,324,949

DATED : June 28, 1994

INVENTOR(S) : Erik Johnsen

It is certified that error appears in the above-identified patent and that said Letters Patent is hereby corrected as shown below:

On the title page, item [56] under Foreign Patent Document, the following should be inserted:

DE 3441856  11/84  Germany

Signed and Sealed this

Fourteenth Day of February, 1995

Attest:

BRUCE LEHMAN

*Attesting Officer*       *Commissioner of Patents and Trademarks*